United States Patent

Matsumoto et al.

(10) Patent No.: US 9,328,137 B2
(45) Date of Patent: May 3, 2016

(54) HYDROGEL-FORMING MATERIAL

(75) Inventors: Keigo Matsumoto, Funabashi (JP); Takeaki Shoji, Funabashi (JP); Tsubasa Kashino, Funabashi (JP); Daiki Yamaguchi, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/113,057

(22) PCT Filed: Apr. 20, 2012

(86) PCT No.: PCT/JP2012/060742
§ 371 (c)(1), (2), (4) Date: Dec. 5, 2013

(87) PCT Pub. No.: WO2012/144609
PCT Pub. Date: Oct. 26, 2012

(65) Prior Publication Data
US 2014/0094420 A1 Apr. 3, 2014

(30) Foreign Application Priority Data
Apr. 22, 2011 (JP) .................................. 2011-096048

(51) Int. Cl.
| | | |
|---|---|---|
| A61K 9/00 | (2006.01) |
| A61K 47/42 | (2006.01) |
| C07K 5/062 | (2006.01) |
| A61K 9/06 | (2006.01) |
| C07K 5/083 | (2006.01) |
| C07K 5/097 | (2006.01) |
| C07K 5/103 | (2006.01) |
| C07K 5/117 | (2006.01) |
| A61K 8/64 | (2006.01) |
| A61Q 19/00 | (2006.01) |
| A61K 8/24 | (2006.01) |
| A61K 8/36 | (2006.01) |
| A61K 8/362 | (2006.01) |
| A61K 8/365 | (2006.01) |
| A61K 8/368 | (2006.01) |

(52) U.S. Cl.
CPC ............... *C07K 5/06026* (2013.01); *A61K 8/24* (2013.01); *A61K 8/36* (2013.01); *A61K 8/362* (2013.01); *A61K 8/365* (2013.01); *A61K 8/368* (2013.01); *A61K 8/64* (2013.01); *A61K 9/06* (2013.01); *A61K 47/42* (2013.01); *A61Q 19/00* (2013.01); *C07K 5/0806* (2013.01); *C07K 5/0821* (2013.01); *C07K 5/1008* (2013.01); *C07K 5/1024* (2013.01); *A61K 2800/48* (2013.01)

(58) Field of Classification Search
None
See application file for complete search history.

(56) References Cited

U.S. PATENT DOCUMENTS

| | | | | |
|---|---|---|---|---|
| 5,587,174 A | * | 12/1996 | Lang ..................... | A61K 8/922 424/401 |
| 2010/0227804 A1 | * | 9/2010 | Sasaki .................. | A61K 9/0024 514/1.2 |
| 2010/0279955 A1 | * | 11/2010 | Miyachi et al. ............. | 514/21.9 |
| 2010/0291210 A1 | | 11/2010 | Miyachi et al. | |
| 2011/0183913 A1 | * | 7/2011 | Miyamoto et al. .......... | 514/18.8 |
| 2012/0035108 A1 | * | 2/2012 | Miyamoto et al. ............ | 514/9.1 |
| 2012/0258059 A1 | * | 10/2012 | Iwama ..................... | A61K 8/64 424/59 |

FOREIGN PATENT DOCUMENTS

| | | |
|---|---|---|
| JP | A-2011-37926 | 2/2011 |
| JP | A-2011-57620 | 3/2011 |
| WO | WO 2009/005151 A1 | 1/2009 |
| WO | WO 2009/005152 A1 | 1/2009 |
| WO | WO 2010/013555 A1 | 2/2010 |
| WO | WO 2010/106981 A1 | 9/2010 |

(Continued)

OTHER PUBLICATIONS

Matsumoto et al., "The Supramolecular Hydrogel Toward "The Smart Biomaterials,"" *Dojin News*, Mar. 2006, No. 118, pp. 1-16 (with Abstract).

(Continued)

*Primary Examiner* — Jeffrey E Russell
(74) *Attorney, Agent, or Firm* — Oliff PLC

(57) ABSTRACT

There is provided a hydrogel-forming material from which a hydrogel can be formed with a simpler method and under milder conditions. A hydrogel-forming material comprising a lipid peptide-type gelator that is formed of at least one selected from compound of the following formula (1):

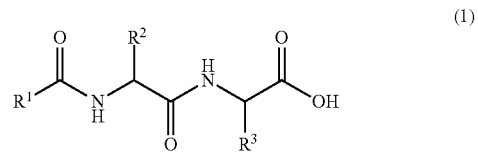

(1)

where $R^1$ is a $C_{9-23}$ aliphatic group; $R^2$ is a hydrogen atom or a $C_{1-4}$ alkyl group which optionally has a $C_{1-2}$ branched chain; $R^3$ is a —$(CH_2)_n$—X group; n is a number from 1 to 4; and X is an amino group, a guanidino group, a —$CONH_2$ group, or a 5-membered ring group or a 6-membered ring group, or a condensed ring group that contains a 5-membered ring and a 6-membered ring, optionally containing 1 to 3 nitrogen atoms, and the similar compounds or pharmaceutically usable salts thereof; water; and an additive including either an organic acid or an organic acid salt.

4 Claims, No Drawings

(56) References Cited

FOREIGN PATENT DOCUMENTS

| WO | WO 2010/147158 A1 | 12/2010 | |
|---|---|---|---|
| WO | WO 2011/052613 A1 * | 5/2011 | A61K 8/64 |

OTHER PUBLICATIONS

Estroff et al., "Water Gelation by Small Organic Molecules," *Chemical Reviews*, Feb. 21, 2004, vol. 104, No. 3, pp. 1201-1217.

Suzuki et al., "Supramolecular Hydrogels Formed by $_L$-Lysine Derivatives," *Chemical Letters*, 2004, vol. 33, No. 11, pp. 1496-1497.

Jung et al., "Self-Assembly of a Sugar-Based Gelator in Water: Its Remarkable Diversity in Gelation Ability and Aggregate Structure," *Langmuir*, Oct. 12, 2001, vol. 17, pp. 7229-7232.

Hamachi et al., "Solid-Phase Lipid Synthesis (SPLS)-2: Incidental Discovery of Organogelators Based on Artificial Glycolipids," *Tetrahedron Letters*, 2001, vol. 42, pp. 6141-6145.

Suzuki et al., "Supramolecular Hydrogel Formed by Glucoheptonamide of $_L$-Lysine: Simple Preparation and Excellent Hydrogelation Ability," *ScienceDirect*, 2007, vol. 63, pp. 7302-7308.

Matsuzawa et al., "Assembly and Photoinduced Organization of Mono— and Oligopeptide Molecules Containing an Azobenzene Moiety," *Advanced Functional Materials*, 2007, vol. 17, pp. 1507-1514.

International Search Report issued in International Patent Application No. PCT/JP2012/060742 dated Jun. 12, 2012.

\* cited by examiner

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Gly Gly Gly His
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2

Gly Gly His Gly
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Gly His Gly Gly
1

<210> SEQ ID NO 4
<211> LENGTH: 4
<212> TYPE: PRT
<213> ORGANISM: Artificial Sequence
```

-continued

```
<220> FEATURE:
<223> OTHER INFORMATION: Synthetic Peptide

<400> SEQUENCE: 4

His Gly Gly Gly
1
```

HYDROGEL-FORMING MATERIAL

TECHNICAL FIELD

The present invention relates to a hydrogel-forming material, specifically, to a hydrogel-forming material from which a hydrogel can be formed with a simple operation; and a hydrogel obtained from the hydrogel-forming material.

BACKGROUND ART

As a material including water as a medium and having high biocompatibility, a hydrogel is used in a wide range of fields, and various kinds of hydrogels including a hydrogel formed of a high molecular weight compound and a hydrogel formed by the self-assembly of a low molecular weight compound have been studied.

Among these, recently, regarding a low molecular weight hydrogelator formed of a low molecular weight compound, the functionality thereof has attracted much attention and the study thereof has been vigorously carried out although it is difficult to elucidate a mechanism for the self-organization of a low molecular weight compound in water; and to make a molecular design. As a result, some low molecular weight hydrogelators have been developed (Non-Patent Documents 1 and 2). Most of the low molecular weight hydrogelators are amphipathic compounds including a long-chain alkyl group, which is a hydrophobic moiety, and a hydrophilic moiety. Examples of the hydrophilic moiety include an amino acid (Non-Patent Document 3), a peptide (Patent Documents 1 and 2), a monosaccharide or a polysaccharide (Non-Patent Documents 4 and 5), and a polyol (Non-Patent Document 6). In addition, a low molecular weight gelator (Non-Patent Document 7) using the fact that a peptide formed of valine is likely to have a β-sheet structure has also been proposed.

In addition, a low molecular weight hydrogelator that can turn an aqueous alcohol solution or an aqueous organic solvent solution into a gel; or a low molecular weight hydrogelator that cannot turn water alone or an organic solvent alone into a gel but can turn an aqueous alcohol solution or an aqueous organic solvent solution into a gel, has been reported.

With such a low molecular weight hydrogelator, a hydrogel can be formed by heating and stirring the hydrogelator and water serving as a medium under a heating condition of about 100° C. to dissolve and disperse the gelator in water; and leaving this solution to stand at room temperature.

SUMMARY OF THE INVENTION

Problem to be Solved by the Invention

As described above, for the above-described low molecular weight hydrogelators which have been proposed so far, for example, a high temperature condition of 100° C. is required for dissolving the hydrogelator in water serving as a medium during hydrogel formation; and the system is required to be sealed and the heating and stirring time is long during heating and stirring. Therefore, in order to industrially produce a hydrogel, production conditions which are extremely disadvantageous from the viewpoints of both cost and operability are required.

The present invention has been made in consideration of the above-described circumstances, and an object thereof is to provide a hydrogel-forming material from which a hydrogel can be formed with a simpler method and under milder conditions.

Means for Solving the Problem

As a result of thorough investigation for solving the above-described problems, the present inventors have found the following. When a hydrogel is formed of: a lipid peptide-type gelator formed of a low molecular weight lipid peptide or a pharmaceutically usable salt thereof; and water, by adding a specific organic acid or a specific organic salt thereto as an additive, the hydrogelator can be dissolved and dispersed in water under a relatively mild temperature condition within a short period of time without sealing the system. Thus, the inventors completed the present invention.

That is, according to a first aspect, the present invention relates to a hydrogel-forming material comprising: a lipid peptide-type gelator that is formed of at least one selected from compounds of the following formulae (1) to (3):

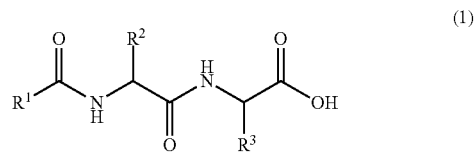

(where $R^1$ is a $C_{9-23}$ aliphatic group; $R^2$ is a hydrogen atom or a $C_{1-4}$ alkyl group which optionally has a $C_{1-2}$ branched chain; $R^3$ is a —$(CH_2)_n$—X group; n is a number from 1 to 4; and X is an amino group, a guanidino group, a —$CONH_2$ group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms),

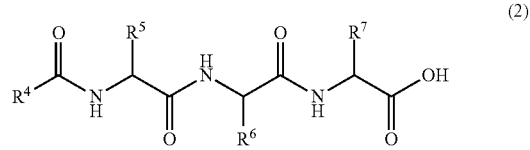

(where $R^4$ is a $C_{9-23}$ aliphatic group; $R^5$ to $R^7$ each independently are a hydrogen atom, a $C_{1-4}$ alkyl group which optionally has a $C_{1-2}$ branched chain, or a —$(CH_2)_n$—X group; n is a number from 1 to 4; and X is an amino group, a guanidino group, a —$CONH_2$ group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms),

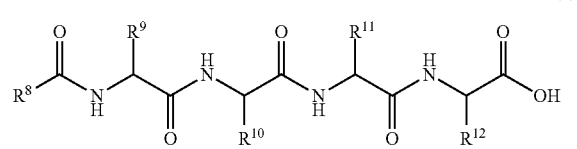

(where $R^8$ is a $C_{9-23}$ aliphatic group; $R^9$ to $R^{12}$ each independently are a hydrogen atom, a $C_{1-4}$ alkyl group which optionally has a $C_{1-2}$ branched chain, or a —$(CH_2)_n$—X group; n is a number from 1 to 4; and X is an amino group, a guanidino group, a —CONH$_2$ group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms), and pharmaceutically usable salts thereof; water; and an additive including either an organic acid or an organic acid salt.

According to a second aspect, the present invention relates to the hydrogel-forming material according to the first aspect, wherein the additive is an additive including either an organic acid or an organic acid salt which has a pH of 6.5 to 9.3 or a pH of 1.8 to 2.5.

According to a third aspect, the present invention relates to the hydrogel-forming material according to the second aspect in which the additive is at least one organic acid selected from a group consisting of acetic acid, lactic acid, succinic acid, tartaric acid, citric acid, trimellitic acid, malic acid, and phosphoric acid, or is at least one organic acid salt selected from a group consisting of an acetate, a lactate, a succinate, a tartrate, a citrate, a trimellitate, a maleate, and a phosphate.

According to a fourth aspect, the present invention relates to a gel which is formed of the hydrogel-forming material according to any one of the first to third aspects.

Effects of the Invention

In the hydrogel-forming material according to the present invention, stirring is performed under a relatively mild temperature condition of 80° C. without sealing the system. As a result, the gelator can be dissolved and dispersed in water within a relatively short period of time to achieve a solution state; and a hydrogel can be easily obtained.

In addition, the lipid peptide-type gelator included in the hydrogel-forming material according to the present invention is an artificial low molecular weight compound which consists only of a lipid and a peptide and thus is extremely safe. In addition, a gel can be formed of the gelator by turning water into a gel without using a crosslinking agent and the like which are required for forming, for example, a synthetic polymer gel proposed in the related art. Therefore, a problem of an unreacted crosslinking agent and the like remaining in the obtained hydrogel does not occur. Furthermore, a hydrogel can be formed by adding the gelator in only about 1% by mass, so load on the environment or load when the gelator enters a living body is small.

Furthermore, the organic acid or the salt thereof that is included, as the additive, in the hydrogel-forming material according to the present invention is widely used as an additive of food products, cosmetic products, and pharmaceutical products.

That is, the hydrogel-forming material according to the present invention has high biological safety and, in particular, is very useful for substrates for cell culture, medical materials, cosmetic product materials, and the like, from the viewpoint of high safety required for the above-described applications.

As described above, the gel according to the present invention can be obtained by the addition of a smaller amount of the gelator compared to that of the related art; and thus is highly safe biologically and environmentally.

Furthermore, as described above, the gel obtained from a lipid peptide which is a low molecular weight compound is easily decomposed by soil bacteria and the like, when used in the external environment, for example in the soil; and is easily decomposed by metabolic enzymes when used in a living body. Therefore, load on the environment and a living body is small.

MODES FOR CARRYING OUT THE INVENTION

The present invention relates to a hydrogel-forming material comprising: a lipid peptide-type gelator that is formed of at least one selected from a compound of the following formula (1) and a pharmaceutically usable salt thereof; water; and an additive including either an organic acid or an organic acid salt.

Hereinbelow, each component will be described.

[Lipid Peptide-Type Gelator]

As the lipid peptide-type gelator used in the present invention, compounds (lipid peptides) of the following formulae (1) to (3) or pharmaceutically usable salts thereof (low molecular weight compounds having a lipid moiety serving as a hydrophobic moiety and a peptide moiety serving as a hydrophilic moiety) can be used.

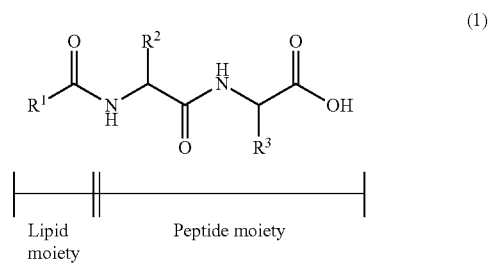

In the formula (1), $R^1$ is a $C_{9-23}$ aliphatic group, and is preferably a linear $C_{11-23}$ aliphatic group which may have 0 to 2 unsaturated bonds.

Specific examples of the lipid moiety (acyl group) including $R^1$ and a carbonyl group adjacent to $R^1$ include a lauroyl group, a dodecylcarbonyl group, a myristoyl group, a tetradecylcarbonyl group, a palmitoyl group, a margaroyl group, an oleoyl group, an elaidoyl group, a linoleoyl group, a stearoyl group, a vaccenoyl group, an octadecylcarbonyl group, an arachidoyl group, an eicosylcarbonyl group, a behenoyl group, an erucanoyl group, a docosylcarbonyl group, a lignoceyl group, and a nervonoyl group. Among these, a lauroyl group, a myristoyl group, a palmitoyl group, a margaroyl group, a stearoyl group, an oleoyl group, an elaidoyl group, and a behenoyl group are preferable.

In the formula (1), $R^2$ included in the peptide moiety is a hydrogen atom or a $C_{1-4}$ alkyl group which may have a $C_{1-2}$ branched chain.

The $C_{1-4}$ alkyl group which may have a $C_{1-2}$ branched chain is an alkyl group which has a $C_{1-4}$ main chain and may have a $C_{1-2}$ branched chain. Specific examples thereof include a methyl group, an ethyl group, an n-propyl group, an i-propyl group, an n-butyl group, an i-butyl group, a sec-butyl group, and a tert-butyl group.

The $R^2$ is preferably a hydrogen atom or a $C_{1-3}$ alkyl group which may have a $C_1$ branched chain and is more preferably a hydrogen atom.

The $C_{1-3}$ alkyl group which may have a $C_1$ branched chain is an alkyl group which has a $C_{1-3}$ main chain and may have a $C_1$ branched chain. Specific examples thereof include a methyl group, an ethyl group, an n-propyl group, an i-propyl group, an i-butyl group, and a sec-butyl group. Among these, a methyl group, an i-propyl group, an i-butyl group, or a sec-butyl group is preferable.

In the formula (1), $R^3$ is a —$(CH_2)_n$—X group. In the —$(CH_2)_n$—X group, n is a number from 1 to 4; and X is an amino group, a guanidino group, a —$CONH_2$ group, or a 5-membered or 6-membered ring which may have 1 to 3 nitrogen atoms, or a condensed heterocyclic ring having a 5-membered ring and a 6-membered ring which may have 1 to 3 nitrogen atoms.

In the —$(CH_2)_n$—X group which is the $R_3$, X is preferably an amino group, a guanidino group, a carbamoyl group (—$CONH_2$ group), a pyrrole group, an imidazole group, a pyrazole group, or an indole group; and is more preferably an imidazole group. In addition, in the —$(CH_2)_n$—X group, n is preferably 1 or 2 and is more preferably 1.

Therefore, the —$(CH_2)_n$ group is an aminomethyl group, a 2-aminoethyl group, a 3-aminopropyl group, a 4-aminobutyl group, a carbamoylmethyl group, a 2-carbamoylethyl group, a 3-carbamoylbutyl group, a 2-guanidinoethyl group, a 3-guanidinobutyl group, a pyrrole methyl group, a 4-imidazolemethyl group, a pyrazole methyl group, or a 3-indole methyl group, is more preferably a 4-aminobutyl group, a carbamoylmethyl group, a 2-carbamoylethyl group, a 3-guanidinobutyl group, a 4-imidazole methyl group, or a 3-indole methyl group, and is still more preferably a 4-imidazole methyl group.

In the compound of the formula (1), a lipid peptide which is particularly preferable for the lipid peptide-type gelator is the following compound including a lipid moiety and a peptide moiety (amino acid assembly moiety). Abbreviations of amino acids are as follows: alanine (Ala), asparagine (Asn), glutamine (Gln), glycine (Gly), histidine (His), isoleucine (Ile), leucine (Leu), lysine (Lys), tryptophan (Trp), and valine (Val). Examples of the compound include Lauroyl-Gly-His, lauroyl-Gly-Gln, lauroyl-Gly-Asn, lauroyl-Gly-Trp, lauroyl-Gly-Lys, lauroyl-Ala-His, lauroyl-Ala-Gln, lauroyl-Ala-Asn, laurayl-Ala-Trp, and lauroyl-Ala-Lys; myristoyl-Gly-His, myristoyl-Gly-Gln, myristoyl-Gly-Asn, myristoyl-Gly-Trp, myristoyl-Gly-Lys, mynstoyl-Ala-His, myristoyl-Ala-Gln, myristoyl-Ala-Asn, myristoyl-Ala-Trp, and myristoyl-Ala-Lys; palmitoyl-Gly-His, palmitoyl-Gly-Gln, palmitoyl-Gly-Asn, palmitoyl-Gly-Trp, palmitoyl-Gly-Lys, palmitoyl-Ala-His, palmitoyl-Ala-Gln, palmitoyl-Ala-Asn, palmitoyl-Ala-Trp, and palmitoyl-Ala-Lys; and stearoyl-Gly-His, stearoyl-Gly-Gln, stearoyl-Gly-Asn, stearoyl-Gly-Trp, stearoyl-Gly-Lys, stearoyl-Ala-His, stearoyl-Ala-Gln, stearoyl-Ala-Asn, stearoyl-Ala-Trp, and stearoyl-Ala-Lys.

Among these, most preferable examples thereof include lauroyl-Gly-His and lauroyl-Ala-His; myristoyl-Gly-His and myristoyl-Ala-His; palmitoyl-Gly-His and palmitoyl-Ala-His; and stearoyl-Gly-His and stearoyl-Ala-His.

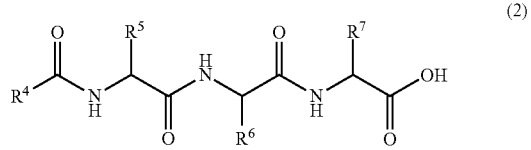

(2)

In the formula (2), $R^4$ is a $C_{9-23}$ aliphatic group. Preferable examples thereof are the same groups as those of the $R^1$.

In the formula (2), $R^5$ to $R^7$ each independently are a hydrogen atom, a $C_{1-4}$ alkyl group which may have a $C_{1-2}$ branched chain, or a —$(CH_2)_n$—X group; and at least one of $R^5$ to $R^7$ is a —$(CH_2)_n$—X group. n is a number from 1 to 4; and X is an amino group, a guanidino group, a —$CONH_2$ group, or a 5-membered or 6-membered ring which may have 1 to 3 nitrogen atoms, or a condensed heterocyclic ring having a 5-membered ring and a 6-membered ring which may have 1 to 3 nitrogen atoms. Preferable examples of the $R^5$ to $R^7$ are the same groups as those of $R^2$ and $R^3$.

In the compound of the formula (2), a preferable lipid peptide is the following compound including a lipid moiety and a peptide moiety (amino acid assembly moiety). Examples of the lipid peptide include myristoyl-Gly-Gly-His, myristoyl-Gly-Gly-Gln, myristoyl-Gly-Gly-Asn, myristoyl-Gly-Gly-Trp, myristoyl-Gly-Gly-Lys, myristoyl-Gly-Ala-His, myristoyl-Gly-Ala-Gln, myristoyl-Gly-Ala-Asn, myristoyl-Gly-Ala-Trp, myristoyl-Gly-Ala-Lys, myristoyl-Ala-Gly-His, myristoyl-Ala-Gly-Gln, myristoyl-Ala-Gly-Asn, myristoyl-Ala-Gly-Trp, myristoyl-Ala-Gly-Lys, myristoyl-Gly-His-Gly, myristoyl-His-Gly-Gly, palmitoyl-Gly-Gly-His, palmitoyl-Gly-Gly-Gln, palmitoyl-Gly-Gly-Asn, palmitoyl-Gly-Gly-Trp, palmitoyl-Gly-Gly-Lys, palmitoyl-Gly-Ala-His, palmitoyl-Gly-Ala-Gln, palmitoyl-Gly-Ala-Asn, palmitoyl-Gly-Ala-Trp, palmitoyl-Gly-Ala-Lys, palmitoyl-Ala-Gly-His, palmitoyl-Ala-Gly-Gln, palmitoyl-Ala-Gly-Asn, palmitoyl-Ala-Gly-Trp, palmitoyl-Ala-Gly-Lys, and palmitoyl-Gly-His-Gly, and palmitoyl-His-Gly-Gly.

Among these, most preferable examples thereof include lauroyl-Gly-Gly-His, myristoyl-Gly-Gly-His, palmitoyl-Gly-Gly-His, palmitoyl-Gly-His-Gly, palmitoyl-His-Gly-Gly, and stearoyl-Gly-Gly-His.

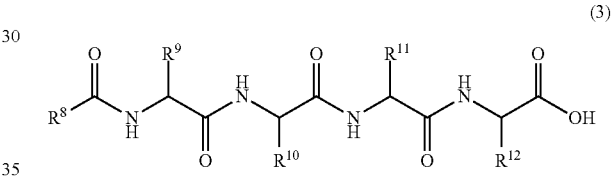

(3)

In the formula (3), $R^8$ is a $C_{9-23}$ aliphatic group. Preferable examples thereof are the same groups as those of the $R^1$.

In the formula (3), $R^9$ to $R^{12}$ each independently are a hydrogen atom, a $C_{1-4}$ alkyl group which may have a $C_{1-2}$ branched chain, or a —$(CH_2)_n$—X group; and at least one of $R^9$ to $R^{12}$ is a —$(CH_2)_n$—X group. n is a number from 1 to 4; and X is an amino group, a guanidino group, a —$CONH_2$ group, or a 5-membered or 6-membered ring which may have 1 to 3 nitrogen atoms, or a condensed heterocyclic ring having a 5-membered ring and a 6-membered ring which may have 1 to 3 nitrogen atoms. Preferable examples of the $R^9$ to $R^{12}$ are the same groups as those of $R^2$ and $R^3$.

Therefore, in the compound of the formula (3), examples of a lipid peptide that is particularly preferable for the lipid peptide-type gelator include lauroyl-Gly-Gly-Gly-His (Gly-Gly-Gly-HIS=SEQ ID NO:1), myristoyl-Gly-Gly-Gly-His (Gly-Gly-Gly-HIS=SEQ ID NO:1), palmitoyl-Gly-Gly-Gly-His (Gly-Gly-Gly-His=SEQ ID NO:1), palmitoyl-Gly-Gly-His-Gly (Gly-Gly-His-Gly=SEQ ID NO:2), palmitoyl-Gly-His-Gly-Gly (Gly-His-Gly-Gly-=SEQ ID NO:3), palmitoyl-His-Gly-Gly-Gly (His-Gly-Gly-Gly-=SEQ ID NO:4), and stearoyl-Gly-Gly-Gly-His (Gly-Gly-Gly-His=SEQ ID NO:1).

In the hydrogel-forming material according to the present invention, the mixing ratio of the lipid peptide-type gelator is, for example, 0.01% by mass to 30% by mass, preferably 0.05% by mass to 10% by mass, and more preferably 0.1% by mass to 5% by mass with respect to the total mass of the hydrogel-forming material.

The lipid peptide-type gelator used in the present invention is formed of at least one selected from compounds (lipid peptides) of the following formulae (1) to (3) and pharmaceutically usable salts thereof. As the hydrogelator, these compounds may be used singly or in a combination of two or more thereof.

[Additives]

As the additive used in the present invention, either an organic acid or an organic acid salt, which is widely used for food products, cosmetic products, and pharmaceutical products, can be used.

Among the additives, in the present invention, either an organic acid or an organic acid salt which has a pH of 6.5 to 9.3 or a pH of 1.8 to 2.5 can be used.

The additive according to the present invention is not particularly limited as long as it is an organic acid or an organic acid salt which has the above-described pH range (6.5 to 9.3 or 1.8 to 2.5). Examples of the organic acid include acetic acid, lactic acid, succinic acid, tartaric acid, citric acid, trimellitic acid, malic acid, and phosphoric acid; and examples of the organic acid salt include an acetate, a lactate, a succinate, a tartrate, a citrate, a trimellitate, a maleate, and a phosphate. Among these, acetic acid, sodium acetate, and phosphoric acid are preferable from the viewpoint of preparing a hydrogel; and citric acid, trisodium citrate, succinate, disodium succinate, and disodium hydrogen phosphate are preferable from the viewpoints of industrial applicability and versatility.

These additives can be used in the form of an organic acid alone, an organic acid salt alone, a mixed acid of two or more organic acids, and a mixed organic acid salt of two or more organic acid salts.

In addition, examples of the organic acid salt include sodium salts and potassium salts. Among these, sodium salts are particularly preferable.

In the hydrogel-forming material according to the present invention, the mixing ratio of the additive is, for example, 0.01% by mass to 10% by mass, preferably 0.05% by mass to 5% by mass, and more preferably 0.05% by mass to 1% by mass with respect to the total mass of the hydrogel-forming material.

[Gel-Forming Material]

The gel-forming material according to the present invention comprises a lipid peptide-type gelator that is formed of at least one selected from compounds of the formulae (1) to (3) and pharmaceutically usable salts thereof; water; and an additive.

In the gel-forming material, by mixing the above-described components and then performing stirring under a temperature condition of about 80° C., the lipid peptide-type gelator can be easily dissolved and dispersed in water, which is a medium.

At this time, the heating and stirring time varies depending on the kinds of the lipid peptide-type gelator and the additive used; and the amounts thereof used; but is normally about 5 minutes to 50 minutes for dissolving and dispersing.

The gel-forming material in the solution state in which the lipid peptide-type gelator is dissolved and dispersed in water is cooled at room temperature (about 25° C.) and is left to stand, thereby obtaining a hydrogel.

[Mechanism for Forming Hydrogel]

When the gel-forming material according to the present invention, in particular, the low molecular weight compound (lipid peptide) of one of the formulae (1) to (3) is put into water and is dissolved and dispersed therein, the peptide moiety of one of the formulae (1) to (3) forms an intermolecular noncovalent bond due to a hydrogen bond. Meanwhile, the lipid moiety of one of the formulae (1) to (3) self-assembles (also referred to as self-organizes) so as to be hydrophobically packed. As a result, a fiber is formed. The shape of the fiber is not limited, and, for example, may be cylindrical or plate-shaped.

When the fiber is formed in water, this fiber forms a three-dimensional network structure. Furthermore, a noncovalent bond is formed between a hydrophilic moiety (peptide moiety) on the fiber surface and the aqueous solvent to cause swelling. As a result, the entire aqueous solution is gelled and thus, a hydrogel is formed.

As described above, the hydrogel-forming material (and the gel obtained from the same) has high biological safety because a low molecular weight gelator formed of natural raw materials such as a fatty acid or an amino acid are used as the gelator; and an organic acid or a salt thereof which is widely used for food products, cosmetic products, or pharmaceutical products is used as the additive.

In addition, in the hydrogel-forming material according to the present invention, by performing stirring under a mild temperature condition of about 80° C. within a short period of time in an open system without sealing the system, the low molecular weight gelator can be easily dissolved and dispersed in water, which is a medium, thereby obtaining a hydrogel.

Accordingly, the hydrogel-forming material according to the present invention is very useful for industrially producing a hydrogel; and can be used as a material in various fields, for example, a substrate for cell culture, a material for storing biomolecules such as cells or proteins, a material for external use, a medical material, a biochemical material, a cosmetic material, a food material, a contact lens, a paper diaper, an artificial actuator, or an agricultural material for a dry land.

EXAMPLES

Hereinbelow, the present invention will be described in detail referring to Examples and Test Examples. However, the present invention is not limited to these examples.

Synthesis Example 1

Synthesis of Lipid Peptide (N-Palmitoyl-Gly-His)

In this example, a lipid peptide used as the gelator was synthesized with the following method.

14.2 g (91.6 mmol) of histidine, 30.0 g (91.6 mmol) of N-palmitoyl-Gly-methyl, and 300 g of toluene were put into a 500 mL four-necked flask, and 35.3 g (183.2 mmol) of 28% methanol solution of sodium methoxide serving as a base was added thereto, followed by heating to 60° C. in an oil bath and stirring for 1 hour. Then, the oil bath was removed, and the solution was allowed to cool to 25° C. This solution was reprecipitated with 600 g of acetone, followed by filtration. The obtained solid matter was dissolved in a mixed solution of 600 g of water and 750 g of methanol. To the solution, 30.5 ml (183.2 mmol) of 6N hydrochloric acid was added to neutralize the solution, and the solid matter was precipitated and separated by filtration. Next, the obtained solid matter was dissolved in a mixed solution of 120 g of tetrahydrofuran and 30 g of water at 60° C.; and 150 g of ethyl acetate was added thereto, followed by cooling from 60° C. to 30° C. Then, the precipitated solid matter was separated by filtration. Furthermore, the obtained solid matter was dissolved in a mixed solvent of 120 g of tetrahydrofuran and 60 g of acetonitrile. The resultant solution was heated to 60° C., was stirred for 1 hour, was cooled, and was filtered. The obtained solid matter was washed with 120 g of water, followed by filtration and drying under reduced pressure. Thus, 26.9 g (yield: 65%) of white crystals of a free form of N-palmitoyl-Gly-His (hereinafter, simply referred to as "N-palmitoyl-Gly-His") was obtained.

Examples 1 to 14

Tests for Evaluating Solubility and Hydrogelation Ability of N-Palmitoyl-Gly-his for Each Additive N-palmitoyl-Gly-His obtained in the above-described synthesis example was added in a screw bottle (manufactured by Maruemu Corporation) such that the concentration of N-palmitoyl-Gly-His was 1.0 wt % (w/w) and the concentration of various additives (an organic acid or an organic acid salt) was 1.0 wt % to 0.05 wt % (w/w), and a stirring bar (manufactured by As One Corporation, 4 mm×10 mm) was put thereinto. Next, heating and stirring were performed, with a cap of the screw bottle being open (that is, an open system), in a water bath (NWB-180N, manufactured by Nissinrika K. K.) for 60 minutes at a maximum until a transparent dispersion state was confirmed at 80° C. For the evaluation of solubility, external appearance after heating and stirring was observed by visual inspection, and cases where the external appearance was transparent were evaluated as ○; and cases where there were undissolved residues were evaluated as x.

Next, the solution was allowed to cool at room temperature overnight. For the evaluation of hydrogelation ability, a state in which the fluidity of the solution was lost after overnight cooling, and even when the screw pipe was inverted, the solution did not flow down, was determined as "Gelation (○)". The final composition after the hydrogelation test and the obtained test results are shown in the following tables.

Example 1

Acetic Acid

TABLE 1

| Composition | Ratio wt % (w/w) | | | |
|---|---|---|---|---|
| N-Palmitoyl-Gly-His | 1.0 | 1.0 | 1.0 | 1.0 |
| Acetic Acid (pH: 2.6) | 1.0 | 0.5 | 0.1 | 0.05 |
| Water | Balance | Balance | Balance | Balance |
| Total Amount | 100 | 100 | 100 | 100 |
| Below, Test Results | | | | |
| Heating and Stirring Time (60 Minutes at Maximum) | 20 minutes | 20 minutes | 20 minutes | 20 minutes |
| Evaluation of Solubility | ○ | ○ | ○ | ○ |
| Evaluation of Hydrogelation Ability | ○ | ○ | ○ | ○ |

Example 2

Sodium Acetate

TABLE 2

| Composition | Ratio wt % (w/w) | | | |
|---|---|---|---|---|
| N-Palmitoyl-Gly-His | 1.0 | 1.0 | 1.0 | 1.0 |
| Sodium Acetate (pH: 7.9) | 1.0 | 0.5 | 0.1 | 0.05 |
| Water | Balance | Balance | Balance | Balance |
| Total Amount | 100 | 100 | 100 | 100 |
| Below, Test Results | | | | |
| Heating and Stirring Time (60 Minutes at Maximum) | 10 minutes | 20 minutes | 30 minutes | 20 minutes |
| Evaluation of Solubility | ○ | ○ | ○ | ○ |
| Evaluation of Hydrogelation Ability | ○ | ○ | ○ | ○ |

Example 3

Phosphoric Acid

TABLE 3

| Composition | Ratio wt % (w/w) | | | |
|---|---|---|---|---|
| N-Palmitoyl-Gly-His | 1.0 | 1.0 | 1.0 | 1.0 |
| Phosphoric Acid (pH: 2.2) | 1.0 | 0.5 | 0.1 | 0.05 |
| Water | Balance | Balance | Balance | Balance |
| Total Amount | 100 | 100 | 100 | 100 |
| Below, Test Results | | | | |
| Heating and Stirring Time (60 Minutes at Maximum) | 20 minutes | 30 minutes | 40 minutes | 60 minutes |
| Evaluation of Solubility | ○ | ○ | ○ | ○ |
| Evaluation of Hydrogelation Ability | ○ | ○ | ○ | ○ |

Example 4

Disodium Hydrogen Phosphate

TABLE 4

| Composition | Ratio wt % (w/w) | | | |
|---|---|---|---|---|
| N-Palmitoyl-Gly-His | 1.0 | 1.0 | 1.0 | 1.0 |
| Disodium Hydrogen Phosphate (pH: 9.1) | 1.0 | 0.5 | 0.1 | 0.05 |
| Water | Balance | Balance | Balance | Balance |
| Total Amount | 100 | 100 | 100 | 100 |

TABLE 4-continued

| Composition | Ratio wt % (w/w) | | | |
|---|---|---|---|---|
| Below, Test Results | | | | |
| Heating and Stirring Time (60 Minutes at Maximum) | 10 minutes | 10 minutes | 25 minutes | 60 minutes |
| Evaluation of Solubility | ○ | ○ | ○ | x |
| Evaluation of Hydrogelation Ability | ○ | ○ | ○ | ○ |

Example 5

Citric Acid

TABLE 5

| Composition | Ratio wt % (w/w) | | | |
|---|---|---|---|---|
| N-Palmitoyl-Gly-His | 1.0 | 1.0 | 1.0 | 1.0 |
| Citric Acid (pH: 2.0) | 1.0 | 0.5 | 0.1 | 0.05 |
| Water | Balance | Balance | Balance | Balance |
| Total Amount | 100 | 100 | 100 | 100 |
| Below, Test Results | | | | |
| Heating and Stirring Time (60 Minutes at Maximum) | 10 minutes | 30 minutes | 60 minutes | 60 minutes |
| Evaluation of Solubility | ○ | ○ | x | x |
| Evaluation of Hydrogelation Ability | ○ | ○ | ○ | ○ |

Example 6

Trisodium Citrate

TABLE 6

| Composition | Ratio wt % (w/w) | | | |
|---|---|---|---|---|
| N-Palmitoyl-Gly-His | 1.0 | 1.0 | 1.0 | 1.0 |
| Trisodium Citrate (pH: 8.1) | 1.0 | 0.5 | 0.1 | 0.05 |
| Water | Balance | Balance | Balance | Balance |
| Total Amount | 100 | 100 | 100 | 100 |
| Below, Test Results | | | | |
| Heating and Stirring Time (60 Minutes at Maximum) | 8 minutes | 15 minutes | 30 minutes | 50 minutes |
| Evaluation of Solubility | ○ | ○ | ○ | ○ |
| Evaluation of Hydrogelation Ability | ○ | ○ | ○ | x |

Example 7

Succinic Acid

TABLE 7

| Composition | Ratio wt % (w/w) | | | |
|---|---|---|---|---|
| N-Palmitoyl-Gly-His | 1.0 | 1.0 | 1.0 | 1.0 |
| Succinic Acid (pH: 2.4) | 1.0 | 0.5 | 0.1 | 0.05 |
| Water | Balance | Balance | Balance | Balance |
| Total Amount | 100 | 100 | 100 | 100 |
| Below, Test Results | | | | |
| Heating and Stirring Time (60 Minutes at Maximum) | 20 minutes | 30 minutes | 60 minutes | 60 minutes |
| Evaluation of Solubility | ○ | ○ | x | x |
| Evaluation of Hydrogelation Ability | ○ | ○ | ○ | ○ |

Example 8

Disodium Succinate

TABLE 8

| Composition | Ratio wt % (w/w) | | | |
|---|---|---|---|---|
| N-Palmitoyl-Gly-His | 1.0 | 1.0 | 1.0 | 1.0 |
| Disodium Succinate (pH: 8.3) | 1.0 | 0.5 | 0.1 | 0.05 |
| Water | Balance | Balance | Balance | Balance |
| Total Amount | 100 | 100 | 100 | 100 |
| Below, Test Results | | | | |
| Heating and Stirring Time (60 Minutes at Maximum) | 10 minutes | 30 minutes | 60 minutes | 60 minutes |
| Evaluation of Solubility | ○ | ○ | x | x |
| Evaluation of Hydrogelation Ability | ○ | ○ | ○ | ○ |

Example 9

Tartaric Acid

TABLE 9

| Composition | Ratio wt % (w/w) | | | |
|---|---|---|---|---|
| N-Palmitoyl-Gly-His | 1.0 | 1.0 | 1.0 | 1.0 |
| Tartaric Acid: (pH 1.9) | 1.0 | 0.5 | 0.1 | 0.05 |
| Water | Balance | Balance | Balance | Balance |
| Total Amount | 100 | 100 | 100 | 100 |

TABLE 9-continued

| Composition | Ratio wt % (w/w) | | | |
|---|---|---|---|---|
| | Below, Test Results | | | |
| Heating and Stirring Time (60 Minutes at Maximum) | 23 minutes | 20 minutes | 60 minutes | 60 minutes |
| Evaluation of Solubility | ○ | ○ | x | x |
| Evaluation of Hydrogelation Ability | ○ | ○ | ○ | ○ |

Example 10

Disodium Tartrate

TABLE 10

| Composition | Ratio wt % (w/w) | | | |
|---|---|---|---|---|
| N-Palmitoyl-Gly-His | 1.0 | 1.0 | 1.0 | 1.0 |
| Disodium Tartrate (pH: 8.4) | 1.0 | 0.5 | 0.1 | 0.05 |
| Water | Balance | Balance | Balance | Balance |
| Total Amount | 100 | 100 | 100 | 100 |
| | Below, Test Results | | | |
| Heating and Stirring Time (60 Minutes at Maximum) | 12 minutes | 30 minutes | 60 minutes | 60 minutes |
| Evaluation of Solubility | ○ | ○ | x | x |
| Evaluation of Hydrogelation Ability | ○ | ○ | ○ | ○ |

Example 11

Lactic Acid

TABLE 11

| Composition | Ratio wt % (w/w) | | | |
|---|---|---|---|---|
| N-Palmitoyl-Gly-His | 1.0 | 1.0 | 1.0 | 1.0 |
| Lactic Acid (pH: 2.2) | 1.0 | 0.5 | 0.1 | 0.05 |
| Water | Balance | Balance | Balance | Balance |
| Total Amount | 100 | 100 | 100 | 100 |
| | Below, Test Results | | | |
| Heating and Stirring Time (60 Minutes at Maximum) | 25 minutes | 50 minutes | 60 minutes | 60 minutes |
| Evaluation of Solubility | ○ | ○ | x | x |
| Evaluation of Hydrogelation Ability | ○ | ○ | ○ | ○ |

Example 12

Sodium Lactate

TABLE 12

| Composition | Ratio wt % (w/w) | | | |
|---|---|---|---|---|
| N-Palmitoyl-Gly-His | 1.0 | 1.0 | 1.0 | 1.0 |
| Sodium Lactate (pH: 6.8) | 1.0 | 0.5 | 0.1 | 0.05 |
| Water | Balance | Balance | Balance | Balance |
| Total Amount | 100 | 100 | 100 | 100 |
| | Below, Test Results | | | |
| Heating and Stirring Time (60 Minutes at Maximum) | 15 minutes | 40 minutes | 60 minutes | 60 minutes |
| Evaluation of Solubility | ○ | ○ | x | x |
| Evaluation of Hydrogelation Ability | ○ | ○ | ○ | ○ |

Example 13

Trimellitic Acid

Example 14

Trisodium Trimellitate

TABLE 13

| Composition | Ratio wt % (w/w) | |
|---|---|---|
| N-Palmitoyl-Gly-His | 1.0 | 1.0 |
| Trimellitic Acid (pH: 1.9) | 1.0 | — |
| Trisodium Trimellitate (pH: 8.4) | — | 1.0 |
| Water | Balance | Balance |
| Total Amount | 100 | 100 |
| | Below, Test Results | |
| Heating and Stirring Time (60 Minutes at Maximum) | 10 minutes | 10 minutes |
| Evaluation of Solubility | ○ | ○ |
| Evaluation of Hydrogelation Ability | ○ | ○ |

As illustrated in Examples 1 to 14, 0.05% (w/w) or greater of acetic acid, sodium acetate, or phosphoric acid, 0.1% (w/w) or greater of disodium hydrogen phosphate, or trisodium citrate, 0.5% (w/w) or greater of citric acid, succinic acid, disodium succinate, tartaric acid, disodium tartrate, lactic acid, or sodium lactate, and 1.0 wt % (w/w) or greater of trimellitic acid or trisodium trimellitate were added as additives, followed by stirring under a mild temperature condition of 80° C. in an open system. As a result, the free form of N-palmitoyl-Gly-His could be easily dissolved in water, which was a medium, so that a transparent liquid could be obtained, and thus, a hydrogel could be obtained.

Comparative Example 1

Test for Evaluating Solubility and Hydrogelation Ability of N-palmitoyl-Gly-His

N-palmitoyl-Gly-His obtained in the above-described synthesis example was added in a screw bottle (manufactured by Maruemu Corporation) such that the concentration of N-palmitoyl-Gly-His was 1.0 wt % (w/w), and a stirring bar (manufactured by As One Corporation, 4 mm×10 mm) was put thereinto. Next, heating and stirring were performed, with a cap of the screw bottle being open, in a water bath (NWB-180N, manufactured by Nissinrika K. K.) for 60 minutes at 80° C. After heating and stirring, undissolved residues were observed by visual inspection.

Then, the solution was allowed to cool at room temperature overnight, and gelation (the state in which the fluidity of the solution was lost; and, even when the screw bottle was inverted, the solution did not flow down) did not occur.

Comparative Example 1

TABLE 14

| Composition | Ratio wt % (w/w) |
|---|---|
| N-Palmitoyl-Gly-His | 1.0 |
| Water | Balance |
| Total Amount | 100 |
| Below, Test Results | |
| Heating and Stirring Time (60 Minutes at Maximum) | 60 minutes |
| Evaluation of Solubility | x |
| Evaluation of Hydrogelation Ability | x |

Comparative Examples 2 and 3

Tests for Evaluating Solubility and Hydrogelation Ability of N-Palmitoyl-Gly-his for Each Additive N-palmitoyl-Gly-His obtained in the above-described synthesis example was added in a screw bottle (manufactured by Maruemu Corporation) such that the concentration of N-palmitoyl-Gly-His was 1.0 wt % (w/w) and the concentration of an additive (sodium ethylenediaminediacetate, sodium ethylenediaminetetraacetate) was 1.0 wt % (w/w), and a stirring bar (manufactured by As One Corporation, 4 mm×10 mm) was put thereinto. The additives (each having a pH that is outside the range of 6.5 to 9.3 or 1.8 to 2.5) are outside the scope of the present invention. Next, heating and stirring were performed, with a cap of the screw bottle being open, in a water bath (NWB-180N, manufactured by Nissinrika K. K.) for 60 minutes at a maximum until a transparent dispersion state was confirmed at 80° C. After heating and stirring, there were no undissolved residues in the solution with sodium ethylenediaminetetraacetate, whereas undissolved residues were observed by visual inspection in the other.

Next, the solution was allowed to cool at room temperature overnight. In any comparative examples, gelation (the state in which the fluidity of the solution was lost; and, even when the screw bottle was inverted, the solution did not flow down) did not occur after overnight cooling.

Comparative Examples 2 and 3

TABLE 15

| Composition | Comparative Example 2 Ratio wt % (w/w) | Comparative Example 3 Ratio wt % (w/w) |
|---|---|---|
| N-Palmitoyl-Gly-His | 1.0 | 1.0 |
| EDTA-2Na (pH: 4.8) | 1.0 | — |
| EDTA-4Na (pH: 9.5) | — | 1.0 |
| Water | Balance | Balance |
| Total Amount | 100 | 100 |
| Below, Test Results | | |
| Heating and Stirring Time (60 Minutes at Maximum) | 60 minutes | 4 minutes |
| Evaluation of Solubility | x | ○ |
| Evaluation of Hydrogelation Ability | x | x |

Comparative Example 4

Tests for Evaluating Solubility and Hydrogelation Ability of N-palmitoyl-Gly-His for Each Additive N-palmitoyl-Gly-His obtained in the above-described synthesis example was added in a screw bottle (manufactured by Maruemu Corporation) such that the concentration of N-palmitoyl-Gly-His was 1.0 wt % (w/w) and the concentration of an additive (sodium dihydrogen phosphate) was 1.0 wt % (w/w), and a stirring bar (manufactured by As One Corporation, 4 mm×10 mm) was put thereinto. The additive (having a pH that is out of the range of 6.5 to 9.3 or 1.8 to 2.5) is outside the scope of the present invention. Next, heating and stirring were performed, with a cap of the screw bottle being open, in a water bath (NWB-180N, manufactured by Nissinrika K. K.) for 60 minutes at a maximum until a transparent dispersion state was confirmed at 80° C. After heating and stirring, there were no undissolved residues in the solution with sodium ethylenediaminetetraacetate, whereas undissolved residues were observed by visual inspection in the other.

Next, the solution was allowed to cool at room temperature overnight. In any comparative examples, gelation (the state in which the fluidity of the solution was lost; and, even when the screw bottle was inverted, the solution did not flow down) did not occur after overnight cooling.

Comparative Example 4

TABLE 16

| Composition | Ratio wt % (w/w) | | | |
|---|---|---|---|---|
| N-Palmitoyl-Gly-His | 1.0 | 1.0 | 1.0 | 1.0 |
| Sodium Dihydrogen Phosphate (pH: 4.6) | 1.0 | 0.5 | 0.1 | 0.05 |
| Water | Balance | Balance | Balance | Balance |
| Total Amount | 100 | 100 | 100 | 100 |

TABLE 16-continued

| Composition | Ratio wt % (w/w) | | | |
|---|---|---|---|---|
| Below, Test Results | | | | |
| Heating and Stirring Time (60 Minutes at Maximum) | 60 minutes | 60 minutes | 60 minutes | 60 minutes |
| Evaluation of Solubility | x | x | x | x |
| Evaluation of Hydrogelation Ability | x | x | x | x |

PRIOR ART DOCUMENTS

Patent Documents

[Patent Document 1] Pamphlet of International Publication No. WO 2009/005151

[Patent Document 2] Pamphlet of International Publication No. WO 2009/005152

Non-Patent Documents

[Non-Patent Document 1] Shinji Matsumoto, Itaru Hamachi, DOJIN NEWS No. 118, 1-16 (2006)

[Non-Patent Document 2] Lara A. Estroff and Andrew D. Hamilton Chemical Review. 2004, 104, 1201-1217

[Non-Patent Document 3] Suzuki, Masahiro. Yumoto, Mariko. Mutsumi, Shirai. Hirofusa, Hanabusa, Kenji. Chemistry Letters, 33(11), 1496-1497

[Non-Patent Document 4] Jong Hwa Jung, Georeg John, Mitsutosish Mausda, Kaname Yoshida, Seiji Shinnkai, and Toshimi Shimizu Langumir 2001, 17, 7229-7232

[Non-Patent Document 5] I. Hamachi, S. Kiyonaka, S. Shinkai, Tetrahedron Lett., 2001, 42, 6141. I. Hamachi, S. Kiyonaka, S, Shinkai, Chem. Commun., 2000, 1281

[Non-Patent Document 6] Masahiro Suzuki, Sanae Owa, Hirofusa Shirai and Kenji Hanabusa, Tetrahedron 2007 63 7302-7308

[Non-Patent Document 7] Yoko Matsuzawa, Katsuyuki Ueki, Masaru Yoshida, Nobuyuki Tamaoki, Tohru Nakamura, Hideki Sakai, and Masahiko Abe, Adv. Funct. Mater. 2007, 17, 1507-1514

The invention claimed is:

1. A hydrogel-forming material comprising:
a lipid peptide-type gelator that is selected from the group consisting of compounds of the following formula (1):

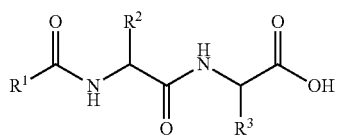
(1)

where
$R^1$ is a $C_{9-23}$ aliphatic group;
$R^2$ is a hydrogen atom or a $C_{1-4}$ alkyl group which optionally has a $C_{1-2}$ branched chain;
$R^3$ is a —$(CH_2)_n$—X group; n is a number from 1 to 4; and
X is an amino group, a guanidino group, a —$CONH_2$ group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms; and pharmaceutically usable salts thereof;
water; and
an additive including either an organic acid or an organic acid salt, wherein
the organic acid is at least one organic acid selected from the group consisting of tartaric acid, trimellitic acid, and malic acid, and
the organic acid salt is at least one organic acid salt selected from the group consisting of a succinate, a tartrate, a trimellitate, and a maleate.

2. A gel which is formed of the hydrogel-forming material according to claim 1.

3. A method of producing a hydrogel-forming material, comprising a step of stirring and heating the following components in an open system, without sealing the open system, where the heating is carried out at 80° C.:
a lipid peptide-type gelator that is selected from compounds of the following formula (1):

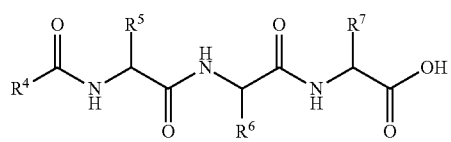
(2)

where
$R^1$ is a $C_{9-23}$ aliphatic group;
$R^2$ is a hydrogen atom or a $C_{1-4}$ alkyl group which optionally has a $C_{1-2}$ branched chain;
$R^3$ is a —$(CH_2)_n$—X group; n is a number from 1 to 4; and
X is an amino group, a guanidine group, a —$CONH_2$ group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms;
and pharmaceutically usable salts thereof;
water; and
an additive including either an organic acid or an organic acid salt, wherein
the organic acid is at least one organic acid selected from the group consisting of tartaric acid, trimellitic acid, and malic acid, and
the organic acid salt is at least one organic acid salt selected from the group consisting of a succinate, a tartrate, a trimellitate, and a maleate.

4. A method of producing a hydrogel, comprising steps of stirring and heating the following components in an open system, without sealing the open system, where the heating is carried out at 80° C.:
a lipid peptide-type gelator that is selected from compounds of the following formula (1):

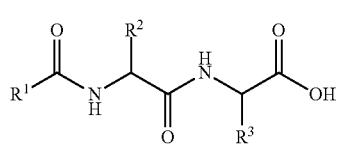
(1)

where
$R^1$ is a $C_{9-23}$ aliphatic group;
$R^2$ is a hydrogen atom or a $C_{1-4}$ alkyl group which optionally has a $C_{1-2}$ branched chain;
$R^3$ is a —$(CH_2)_n$—X group; n is a number from 1 to 4; and
X is an amino group, a guanidine group, a —$CONH_2$ group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms;
and pharmaceutically usable salts thereof;
water; and
an additive including either an organic acid or an organic acid salt, wherein the organic acid is at least one organic acid selected from the group consisting of tartaric acid, trimellitic acid, and malic acid, and the organic acid salt is at least one organic acid salt selected from the group consisting of a succinate, a tartrate, a trimellitate, and a maleate; and allowing to cool.

* * * * *